United States Patent [19]
Augais et al.

[11] Patent Number: 5,579,361
[45] Date of Patent: Nov. 26, 1996

[54] RADIODIAGNOSIS APPARATUS OF THE CHARGE TRANSFER DETECTOR TYPE

[75] Inventors: Thierry Augais, Gif sur Yvette; Manuel Thorez, Brie sur Marne, both of France

[73] Assignee: Trophy Radiologie, Vincennes, France

[21] Appl. No.: 453,699

[22] Filed: May 30, 1995

[30] Foreign Application Priority Data

May 31, 1994 [FR] France ................................. 94 06628

[51] Int. Cl.$^6$ ........................................................ A61B 6/14
[52] U.S. Cl. ............................................. 378/38; 378/98.8
[58] Field of Search ............................... 378/38–40, 98.8

[56] References Cited

U.S. PATENT DOCUMENTS 4,995,062   5/1994   Scheelze-Ganzlin .................. 378/40

FOREIGN PATENT DOCUMENTS

0366235B1   8/1989   European Pat. Off. .
90/14793   12/1990   WIPO .

Primary Examiner—Craig E. Church
Attorney, Agent, or Firm—Pennie & Edmonds

[57] ABSTRACT

A radiodiagnosis apparatus for taking panoramic and tomographic pictures of an object, comprising an X-ray source and an X-ray receiver with a secondary slot for the passage of the received X-rays and downstream of a scintillator screen converting received X-rays into visible light, a sensor for transferring electric charges stored in the image elements from one line to the next one, fixedly mounted in the receiver to have its image zone corresponding to the opening of the secondary slot, means for controlling the charge transfer by the shift of the lines of charge at a frequency simulating the motion of a conventional radiographic film behind the secondary slot and a data processing device, the control means comprising a part movable behind the secondary slot at the speed of a radiographic film and a detector for the speed of that movable part and a unit converting the detected speed into an equivalent frequency of line shift of the charge transfer sensor.

6 Claims, 1 Drawing Sheet

U.S. Patent
Nov. 26, 1996
5,579,361
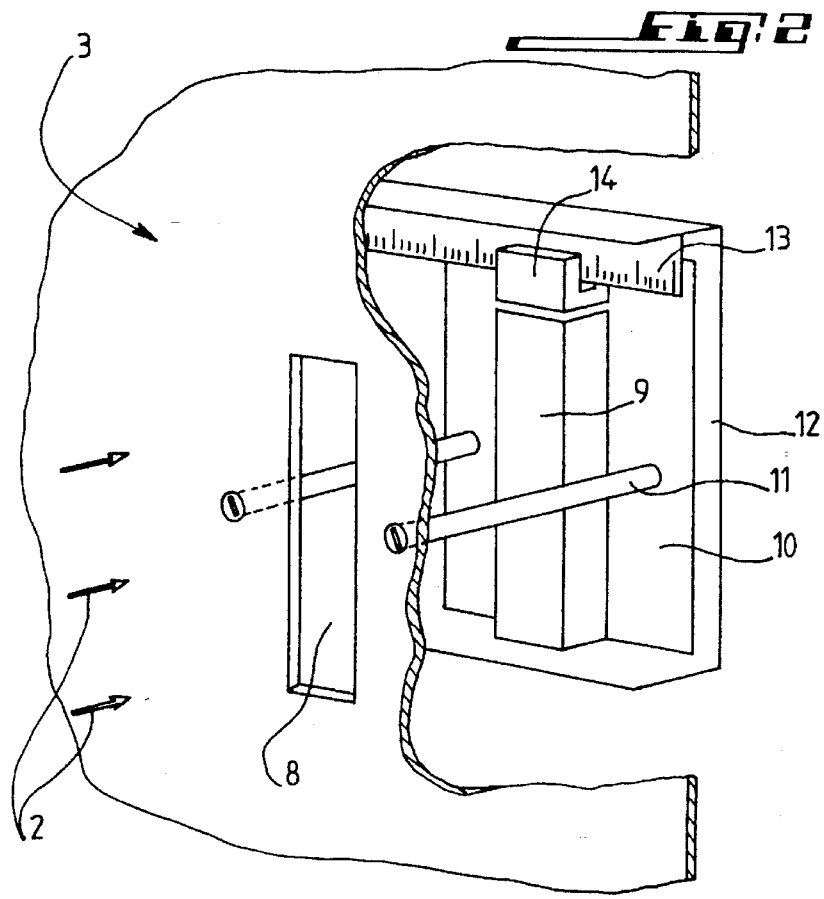
Fig. 2
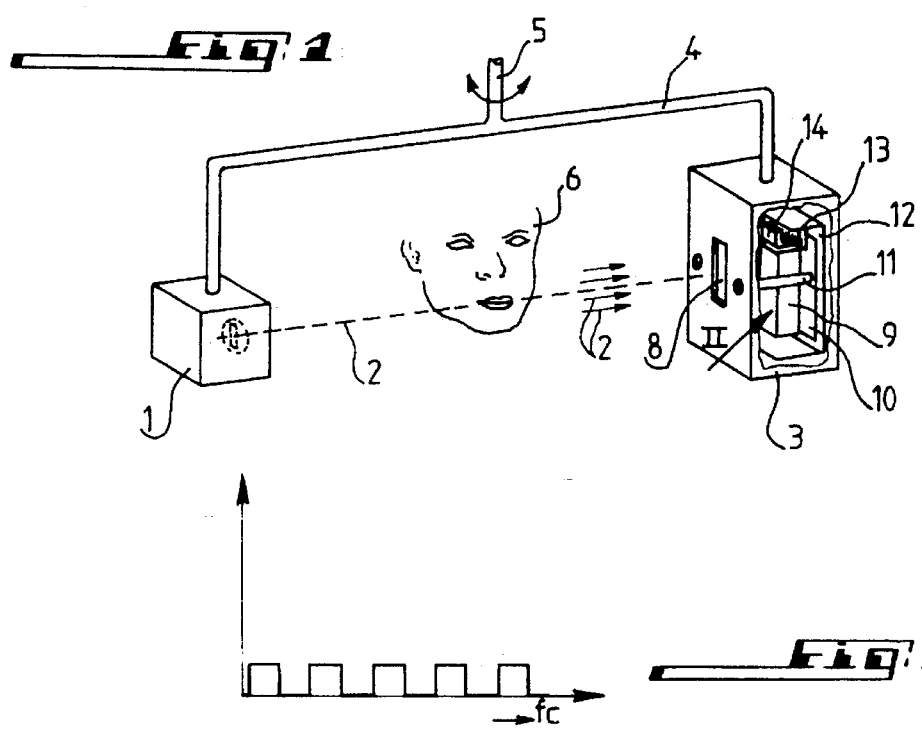
Fig. 1
Fig. 3

RADIODIAGNOSIS APPARATUS OF THE CHARGE TRANSFER DETECTOR TYPE

SUMMARY OF THE INVENTION

The invention relates to a radiodiagnosis apparatus for taking panoramic and advantageously tomographic radiographic of an object such as a jaw of a patient, of the type comprising a source of X-rays and a receiver of the X-rays having passed through the object, the receiver comprising a secondary slot for the passage of the received X-rays and downstream of a scintillator transforming the X-rays into visible light, a sensor of the type with coupled charges and with a reading through transfer of electrical charges produced in the image elements from one line into the following line and fixedly mounted in the receiver so that its image zone corresponds to the opening of the secondary slot, means for controlling the transfer of charges through shift of the lines of charges at a frequency simulating the displacement of a conventional radiographic film behind the secondary slot, a device for the processing of the data supplied by the sensor and a device for reproducing images.

The radiodiagnosis apparatuses of this kind which are known exhibit the inconvenience that they are incompatible with the conventional radiodiagnosis apparatuses which use radiographic films with a linear or rotary displacement, included in a film-carrying cassette or drum. This incompatibility is due to the provision of the means for the control of the shift of the lines of charges.

Therefore a physician which wishes to have available an apparatus bringing about the advantages provided by a detector of the charge-coupled type is compelled to replace his conventional radiographic film apparatus with a new specific apparatus fitted with a charge-coupled sensor.

The object of the invention is to avoid this inconvenience and to provide an apparatus making use of a sensor forming a device with transfer of charges or a so-called charge-coupled device or CCD which is compatible with the conventional apparatus.

To reach this goal the apparatus according to the invention is characterized in that the shift-control means comprise one portion moving behind the secondary slot with a speed at which would move a radiographic film, a detector of the speed of displacement of this portion and a unit for the conversion of the speed thus established into an equivalent frequency of shift of the lines of the charge-transfer sensor.

The invention will be better understood and further objects, characterizing features, details and advantages thereof will appear more clearly as the following explanatory description proceeds with reference to the accompanying diagrammatic drawings given by way of non-limiting example only illustrating a presently preferred specific embodiment of the invention and in which:

BRIEF DESCRIPTION OF THE DRAWINGS

FIG. 1 is a simplified diagrammatic perspective view of a radiodiagnosis apparatus according to the present invention;

FIG. 2 is a view on a larger scale with parts broken away of the detail shown at II on FIG. 1; and FIG. 3 illustrates the output signals of the detector of the speed of the shift control means according to the present invention.

DETAILED DESCRIPTION OF THE INVENTION

The invention will be described by way of non-limiting example in its application to a dental radiodiagnosis apparatus intended to produce panoramic tomographic radiographies of the jaw of a patient. As it appears from FIG. 1 such an apparatus essentially comprises a device forming a source 1 of the X-rays 2, a receiver 3 of the X-rays as well as an arm 4 for supporting the source device and the receiver, which is mounted for rotation about a vertical shaft 5 arranged so that the apparatus may turn around the head of the patient 6 whose jaw has the X-rays passing therethrough.

The X-rays emitter device 1 is of a type known per se and needs not to be described in greater detail.

The receiver 3 comprises as known a secondary slit 8 through which the X-rays 2 which have passed through the jaw and thus contain the data of the panoramic radiographic pictures enter the receiver to reach a sensor 9 made as a charge transfer device through the medium of a scintillator screen known per se and not shown. The sensor 9 is made fast to the stationary part 10 the mechanical offset of which with respect to the slit is provided by mechanical means 11.

The sensor 9 of the charge transfer type called CCD is known per se also and does not require a detailed explanation. It suffices to recall that it is of the matric type sensitive to the X-rays and adapted to integrate the information constituted by the attenuations of the X-rays having passed through the jaw locally through accumulation of electric charges in the photosites of the sensor which constitute the image elements and are located in the extension of the photo-electric impact point. The reading of the sensor is effected through transfer of the charges of one line of image elements into the neighbouring line and this up to the edge of the image zone. The last line of image elements is transferred into a shift register which is then emptied element by element into an output amplifier. Each image element is then converted after amplification and then stored for the purpose of its presentation or of its digital processing. This treatment does not form part of the present invention; it is known and will therefore not be described.

The peculiarity of the invention resides in the fact that the receiver comprises a movable part 12 which is adapted to be driven at the speed of a conventional radiographic film. For that purpose this movable part may be displaced according to a translatory motion in the cassette-carrier of a conventional apparatus for a radiographic film exactly like a cassette by sliding on the stationary part 12. The movable part may exhibit the overall size of a standard film—carrying cassette.

To determine the speed of the movable part 12, the latter is provided with a graduated scale 13 arranged so as to pass in front of a detector 14 for the travelling of the said graduations, made fast to the stationary part. The detector 14 is provided as an incremental encoder.

It is easily understood that the incremental encoder detector 14 produces a signal in the shape of a sequence of pulses shown on FIG. 3 when the graduated scale 13 travels past it during the displacement of the movable part 12. The frequency $f_c$ of the signal produced by the incremental encoder detector 14 depends of the space resolution of the latter. The frequency of the control of the shift of the lines of the CCD sensor with respect to the frequency $f_c$ is determined by the dimensions of the image elements of the sensor and may be expressed by the relation:

$$f_d = r/l \cdot f_c$$

r essentially being the graduation pitch of the scale and l designating the width of an image element.

The shift control signal having the shift frequency $f_d$ is generated by a suitable device (not shown) connected to the detector 14. Thus every time the movable part 12 has moved over a length equivalent to the width of an image element, the lines of the sensor are shifted by one position.

In the example shown the speed detector 14 is provided as an optical incremental encoder. The detector may of course be provided in any other suitable form, for example as a Hall-effect encoder.

The detector 14 may be adapted to measure angular displacements of the movable part 12 and thus permits the application of the invention to orthopantomographic apparatus with a rotary drum.

It results from the description which has just been made that the invention may be used in orthopantomographic apparatus available on the market and designed for using radiographic films with a linear or rotary displacement while making use of the advantages of the sensors of the charge-transfer type.

We claim:

1. A radiodiagnosis apparatus for making panoramic and advantageously tomographic radiographic pictures of an object such as the jaw of a patient, of the type comprising a source of X-rays and a receiver of the X-rays having passed through said object, the receiver comprising a secondary slot for the passage of the received X-rays and downstream of a scintillator screen transforming these received X-rays into visible light, a sensor of the charge-transfer device type provided to be read through transfer of the electric charges accumulated in the image elements from one line into the next line, which is fixedly mounted in the receiver so that its image zone corresponds to the opening of the secondary slot, means for the control of the transfer of the charges by the shift of the lines of charges, at a frequency simulating the displacement of a conventional radiographic film behind the secondary slot, a device for the processing of the data supplied by the sensor and an image reproducing device, wherein the improvement consists in that the shift control means comprise a movable part moving behind the secondary slot at a speed at which a radiographic film would move and a detector of the speed of displacement of this movable part as well as a unit for the conversion of the speed thus established into an equivalent frequency of the shift of the lines of the charge transfer sensor.

2. An apparatus according to claim 1, wherein the movable part comprises an element such as a graduated scale arranged so as to travel past the detector during the displacement of the movable part and the detector is adapted to produce a signal the frequency of which is a function of the graduation of the graduated scale element, which is transmitted to the aforesaid conversion unit.

3. An apparatus according to claim 2, wherein the detector is provided as an optical incremental encoder.

4. An apparatus according to claim 2, wherein the detector is of the Hall-effect encoder type.

5. An apparatus according to claim 2, wherein the conversion unit is adapted to produce from the signal at the frequency produced by the detector, the shift signal by taking into account the pitch of the encoder detector and the width of the image elements of the sensor.

6. An apparatus according to claim 5, wherein the frequency of the shift signal and the frequency of the signal produced by the detector meet the equation $f_d = r/l \cdot f_c$ wherein r and l designate the pitch of the graduation of the graduated scale and the width of an image element, respectively.

* * * * *